United States Patent
Ueno et al.

(10) Patent No.: US 7,304,182 B2
(45) Date of Patent: Dec. 4, 2007

(54) CRYSTALLINE PARAHYDROXYBENZOIC ACID ANHYDRIDE AND PROCESS FOR PREPARING THE SAME

(75) Inventors: Ryuzo Ueno, Nishinomiya (JP); Masaya Kitayama, Takarazuka (JP); Nobutaka Izumichi, Ashiya (JP); Masaharu Kittaka, Takarazuka (JP)

(73) Assignee: Kabushiki Kaisha Ueno Seiyaku Oyo Kenkyujo, Osaka (JP)

( * ) Notice: Subject to any disclaimer, the term of this patent is extended or adjusted under 35 U.S.C. 154(b) by 13 days.

(21) Appl. No.: 10/553,451

(22) PCT Filed: Apr. 12, 2004

(86) PCT No.: PCT/JP2004/005213

§ 371 (c)(1), (2), (4) Date: Oct. 17, 2005

(87) PCT Pub. No.: WO2004/092107

PCT Pub. Date: Oct. 28, 2004

(65) Prior Publication Data

US 2006/0264670 A1    Nov. 23, 2006

(30) Foreign Application Priority Data

Apr. 17, 2003  (JP) .............................. 2003-112494

(51) Int. Cl.
*C07C 51/56* (2006.01)
(52) U.S. Cl. ...................................................... 562/895
(58) Field of Classification Search ................. 562/895
See application file for complete search history.

(56) References Cited

U.S. PATENT DOCUMENTS 4,814,498 A * 3/1989 Cocco ........................ 562/475

FOREIGN PATENT DOCUMENTS

JP    2002-316969 A    10/2002

* cited by examiner

*Primary Examiner*—Yvonne Eyler
*Assistant Examiner*—M Louisa Lao
(74) *Attorney, Agent, or Firm*—Sughrue Mion, PLLC

(57) ABSTRACT

The present invention provides a process for preparing crystalline parahydroxybenzoic acid anhydride, comprising the step of precipitating and isolating parahydroxybenzoic acid in an aqueous solvent at a temperature equal to or above the transition temperature of parahydroxybenzoic acid.

10 Claims, 2 Drawing Sheets

CRYSTALLINE PARAHYDROXYBENZOIC ACID ANHYDRIDE AND PROCESS FOR PREPARING THE SAME

TECHNICAL FIELD

The present invention relates to crystalline parahydroxybenzoic acid anhydride and a process for preparing the same.

BACKGROUND ART

Parahydroxybenzoic acid has been used for manufacturing a wide variety of products including liquid crystalline polymers and preservatives for cosmetics and medicines. Generally, parahydroxybenzoic acid is prepared by a method in which phenol is reacted with potassium hydroxide to give potassium phenoxide, and the obtained potassium phenoxide is reacted with carbon dioxide under pressure to give potassium parahydroxybenzoate and then, parahydroxybenzoic acid is isolated by means of aciding out procedure, i.e. by adding a mineral acid to the salt.

For a long time, the Kolbe-Schmitt reaction, a solid-gas phase reaction, had been employed for the reaction between potassium phenoxide and carbon dioxide. This reaction, however, has several problems such as the long reaction time, the high amount waste of the starting materials in the side reaction, and the difficulty of attaining a stable yield. In order to solve those problems, a number of methods have been proposed.

One of the inventors has proposed a process for preparing parahydroxybenzoic acid, which comprises the step of reacting potassium phenoxide with carbon dioxide in the presence of an appropriate solvent in a suspension at a temperature equal to or more than 180° C., wherein phenol in an amount required for reacting with dipotassium parahydroxybenzoate to give potassium phenoxide is added to the reaction before the initiation of the carboxylation step. The process can produce potassium parahydroxybenzoate in a short time with high yield in a continuous manner (Japanese Patent Publication (KOKOKU) No. 9529/1970).

Parahydroxybenzoic acid can be obtained by precipitating the resulting potassium parahydroxybenzoate with acid. Thus obtained parahydroxybenzoic acid is then isolated from the solution by filtration with the aid of centrifugation, washed with water, and dried to be used as a starting material for manufacturing, for example, liquid crystalline polymers.

Parahydroxybenzoic acid, however, is highly soluble in aqueous solvent and therefore the yield of the product is low when the precipitated product is collected from aqueous solvent, e.g., by precipitation with acid. For this reason, to improve the yield, the solution containing parahydroxybenzoic acid is usually cooled to around room temperature to give slurry and then centrifuged to collect parahydroxybenzoic acid. The resulting product is crystalline parahydroxybenzoic acid monohydrate containing a lot of water which comes from the hydrated water and the aqueous solvent. It brings the necessity of a lot of energy to eliminate the water in the drying step, resulting in the high production cost and the long processing time.

In addition, the size of the obtained crystal is small. When thus obtained crystals are added into a reaction vessel as a starting material for manufacturing liquid crystalline polymers or the like, fine particles of parahydroxybenzoic acid fly in the air as powder dust, and t therefore they are difficult to handle.

DISCLOSURE OF THE INVENTION

Problem to be Solved by the Invention

An object of the present invention is to provide a process for preparing parahydroxybenzoic acid having good powder characteristics in a short time with low production cost.

MEANS FOR SOLVING THE PROBLEM

The present invention provides a process for preparing crystalline parahydroxybenzoic acid anhydride, comprising the step of precipitating and isolating parahydroxybenzoic acid in an aqueous solvent at a temperature equal to or above the transition temperature of parahydroxybenzoic acid.

In the present invention, "precipitating" means depositing crystalline parahydroxybenzoic acid from a solution or a suspension containing parahydroxybenzoic acid to give crystalline product.

"Transition temperature of parahydroxybenzoic acid" means the temperature at which parahydroxybenzoic acid in an aqueous solvent changes from anhydride to hydrate.

The present invention also provides a process for preparing crystalline parahydroxybenzoic acid anhydride, comprising the step of precipitating and isolating parahydroxybenzoic acid with acid from a solution of parahydroxybenzoate in an aqueous solvent at a temperature equal to or above the transition temperature of parahydroxybenzoic acid.

Further, the present invention provides a process for preparing crystalline parahydroxybenzoic acid anhydride, comprising the steps of precipitating parahydroxybenzoic acid with acid in an aqueous solvent, heating the parahydroxybenzoic acid precipitates to dissolve the same, re-precipitating and isolating the parahydroxybenzoic acid at a temperature equal to or above the transition temperature of parahydroxybenzoic acid.

The present invention also provides a process for preparing crystalline parahydroxybenzoic acid anhydride, comprising the steps of preparing a solution of parahydroxybenzoic acid in an aqueous solvent, and precipitating and isolating the parahydroxybenzoic acid at a temperature equal to or above the transition temperature of parahydroxybenzoic acid.

Further, the present invention provides a process for preparing crystalline parahydroxybenzoic acid anhydride, comprising the steps of preparing a suspension of parahydroxybenzoic acid in an aqueous solvent, heating the suspension to a temperature equal to or above the transition temperature of parahydroxybenzoic acid, and isolating the crystalline parahydroxybenzoic acid anhydride at a temperature equal to or above the transition temperature of parahydroxybenzoic acid.

The present invention also provides crystalline parahydroxybenzoic acid anhydride obtained by the process of the present invention.

THE EFFECT OF THE INVENTION SUPERIOR TO THE CONVENTIONAL ART

According to the present invention, crystalline parahydroxybenzoic acid anhydride with relatively large crystal size can be obtained by the process which requires smaller amount of heat in the drying step than that required in conventional processes for preparing crystalline parahydroxybenzoic monohydrate.

BEST MODE FOR CARRYING OUT THE INVENTION

Figure 1:
FIG. 1 is the micrograph showing crystalline parahydroxybenzoic acid obtained in Example 3.

As described above, the transition temperature of parahydroxybenzoic acid is the temperature at which parahydroxybenzoic acid in an aqueous solvent changes from anhydride to hydrate.

It means that parahydroxybenzoic acid is present in an aqueous solvent in the form of hydrate at a temperature below the transition temperature, and of anhydride at a temperature above the same.

The transition temperature of parahydroxybenzoic acid in water is around 52 to 54° C. When a mixture of water and an aqueous organic solvent is used, the transition temperature is slightly different depending on the type and concentration of the organic solvent. The skilled in the art, however, can determine the transition temperature by measuring in advance the temperature at which parahydroxybenzoic acid changes the form.

Crystalline parahydroxybenzoic acid anhydride can be obtained by conducting the precipitation and isolation at a temperature equal to or above the transition temperature. At the same time, too high temperature causes heat loss and high production cost. The precipitation and isolation are, therefore, preferred to be performed at a temperature in the range from the transition temperature to the temperature +30° C., preferably +20° C.

Specifically, the process of the present invention may be described as the following embodiments.

(1) A process that comprises precipitating parahydroxybenzoic acid, for example, by using acid, in an aqueous solvent at a temperature equal to or above the transition temperature of parahydroxybenzoic acid. That is, the process which comprises the steps of reacting potassium phenoxide with carbon dioxide, and then precipitating and isolating parahydroxybenzoic acid at a temperature equal to or above the transition temperature of parahydroxybenzoic acid.

According to this process, crystalline parahydroxybenzoic acid anhydride can be easily obtained just by performing the precipitating and isolating steps in the conventional process at a high temperature.

(2) A process that comprises precipitating parahydroxybenzoic acid with acid in an aqueous solvent, heating the parahydroxybenzoic acid precipitates to dissolve the same and then re-precipitating and isolating the parahydroxybenzoic acid at a temperature equal to or above the transition temperature of parahydroxybenzoic acid. That is, the process in which parahydroxybenzoic acid is precipitated with acid (to give crystalline monohydrate) from a solution of parahydroxybenzoate in an aqueous solvent at a low temperature that is used in a conventional method, such as about 20° C., and the precipitate is heated to a high temperature, such as about 90° C., to dissolve, and then the parahydroxybenzoic acid is re-precipitated and isolated at a temperature equal to or above the transition temperature of parahydroxybenzoic acid.

According to this process, wherein parahydroxybenzoic acid precipitated with acid at a low temperature is dissolved and then re-precipitated, crystalline parahydroxybenzoic acid anhydride having a very high purity can be obtained.

(3) A process that comprises dispersing parahydroxybenzoic acid in an aqueous solvent, heating the dispersion to give a solution, and then precipitating and isolating the parahydroxybenzoic acid from the solution at a temperature equal to or above the transition temperature of parahydroxybenzoic acid.

According to this process, wherein parahydroxybenzoic acid is once dissolved at a high temperature such as 90° C. and then isolated as crystalline product at a temperature equal to or above the transition temperature of parahydroxybenzoic acid, crystalline parahydroxybenzoic acid anhydride can be easily obtained from parahydroxybenzoic acid independent of the method used in preparing the starting parahydroxybenzoic acid and its crystal form.

(4) A process that comprises preparing a suspension of parahydroxybenzoic acid in an aqueous solvent, heating the suspension to the temperature equal to or above the transition temperature of parahydroxybenzoic acid, and isolating the crystalline parahydroxybenzoic acid anhydride at a temperature equal to or above the transition temperature of parahydroxybenzoic acid.

According to this process, wherein the suspension containing parahydroxybenzoic acid in an aqueous solvent at a temperature below the transition temperature is heated to a temperature equal to or above the transition temperature of parahydroxybenzoic acid and then the parahydroxybenzoic acid is isolated, parahydroxybenzoic acid anhydride can be easily obtained from parahydroxybenzoic acid independent of the method used in preparing the starting parahydroxybenzoic acid and its crystal form.

When the process comprises the step of precititation with acid in the above embodiments of the present invention, parahydroxybenzoate used in the step, which is provided as a solution in an aqueous solvent, is not particularly limited.

The solution of parahydroxybenzoate in an aqueous solvent which is preferably used may be a solution of potassium parahydroxybenzoate in an aqueous solvent that may be obtained by reacting potassium phenoxide with carbon dioxide, or a solution of sodium parahydroxybenzoate or ammonium parahydroxybenzoate in an aqueous solvent that is prepared by dissolving parahydroxybenzoic acid obtained by a conventional method in an aqueous solvent with the aid of a basic substance such as sodium hydroxide, sodium carbonate, sodium bicarbonate, or ammonia.

Among the above, potassium parahydroxybenzoate in an aqueous solvent is particularly preferred.

The acid used for the precipitation is not particularly limited, and an inorganic or organic acid may be used. Examples of inorganic acids include binary acids (hydrogen acids) such as hydrochloric acid and hydrofluoric acid, and oxo acids such as nitric acid, sulfuric acid, phosphoric acid, and perchloric acid. Examples of organic acids include formic acid and acetic acid. Among them, sulfuric acid is preferably used. The pH in the step may be adjusted to 1-4 by means of the acids as described above.

As the aqueous solvent in the present invention, water may be used either alone or as a mixture with an aqueous organic solvent, for example lower alcohols such as methanol, ethanol, and isopropanol. Preferably, water is used alone because it is cheaper compared to organic solvent and the collection rate of parahydroxybenzoic acid from the aqueous solvent in the isolating step is high.

When the aqueous solvent is a mixture of water and an aqueous organic solvent, the mixed solvent preferably contain water more than 70% by weight, more preferably 80% by weight.

The amount of the aqueous solvent used is preferably 3 to 15, more preferably 4 to 10 times the amount of the crystalline parahydroxybenzoic acid by weight.

The method for reacting potassium phenoxide with carbon dioxide is not particularly limited, and any conventional method may be used. For example, it is the method in which carbon dioxide is dispersed into a liquid mixture containing 0.05 to 3 moler parts of an aromatic hydroxyl compound, such as phenol, per 1 molar part of potassium phenoxide in the presence of reaction medium, and reacted with potassium phenoxide at a temperature equal to or above 150° C.

The reaction between potassium phenoxide and carbon dioxide is preferred to be performed at a temperature from 150 to 350° C., preferably from 200 to 320° C., under a carbon dioxide pressure from 0.1 to 2 MPa (G), preferably from 0.2 to 1.6 MPa (G), wherein the pressure is defined according to the reaction temperature.

For example, when the reaction temperature is 260° C. or 280° C., the carbon dioxide pressure is preferred to be 0.2 to 0.7 MPa (G) or 0.2 to 1 MPa (G), respectively.

The reaction medium used in the reaction between potassium phenoxide and carbon dioxide may be any conventional solvent provided that potassium phenoxide does not substantially dissolve in the solvent. For example, light oil, kerosene, gasoline, lube oil, alkylbenzenes, alkyl naphthalenes, diphenyl ether, diphenyl dialkanes, terphenyl compounds, hydrogenated terphenyl compounds, diphenyl ether, alkyl phenyl ethers, and a mixture thereof may be used.

The reaction medium may be usually used in an amount equal to or more than 0.5 times, preferably 0.5 to 10 times, the amount of potassium phenoxide by weight. When the reaction medium is also used in the steps of preparing the potassium phenoxide (i.e., in the reaction between phenol and an alkaline compound) and/or dehydrating the same, the reaction medium is preferably used in an amount enough to cover the amount of the reaction medium which will disappear upon boiling with water.

In the above reaction between potassium phenoxide and carbon dioxide performed in the presence of the reaction medium under heat and pressure, side products produced in the reaction solution as well as water, which are present in the liquid phase, can be transferred to the gas phase and removed from the reaction system. This procedure can improve the yield of the reaction product.

After the reaction between potassium phenoxide and carbon dioxide completes, the reaction mixture is cooled and added with water to be separated into a reaction medium phase and an aqueous phase. If necessary, the reaction medium phase may be washed by water.

The aqueous phase described above is applied to extraction by a hydrophobic organic solvent at a temperature equal to or below 110° C. The solvent used in the extraction may be hydrocarbons, halogenated hydrocarbons, nitrated hydrocarbons, ethers, ketones, and alcohols having a carbon number of 4 or more, such as xylene, toluene, dichloromethane, nitrobenzene, diethyl ether, methyl isobutyl ketone, and 2-ethyl hexyl alcohol. The volume of the solvent used for the extraction is preferred to be 0.3 to 2 times that of the aqueous phase, and the temperature for the extraction is preferably 30 to 110° C.

Phenol in the reaction medium phase is preferred to be directly reused in the next reaction. Alternatively, the phenol may be recovered as a solution of potassium phenoxide, by means of the reaction of the phenol in the reaction medium phase and the extracted phase with a solution of potassium hydroxide. The phenol and the solution of potassium phenoxide thus collected may get back to the step of preparing the starting material to be used circularly.

The parahydroxybenzoic acid precipitated by the process of the present invention is then isolated from the mother liquid by centrifugation (i.e., dehydrated). In the present invention, the isolating step is also performed at a temperature equal to or above the transition temperature of parahydroxybenzoic acid. Further, the following drying step is also preferably performed at a temperature equal to or above the transition temperature of parahydroxybenzoic acid.

Following the isolating step, the parahydroxybenzoic acid obtained by the process of the present invention is dried in the drying step. The resulting crystalline product is anhydride and contains small amount of water. Therefore, the amount of water to be removed in the drying step is small. In addition, there is no need for energy to eliminate the hydrated water. As a result, the load on the drying machine is reduced and the drying step can be significantly simplified.

If the isolating and/or drying steps are performed at a temperature below the transition temperature, crystalline parahydroxybenzoic acid changes from anhydride to hydrate in the centrifuge and/or the drying machine. Because of this, problems relating to aggregation of the isolated crystalline product and necessity of a large amount of energy in the drying step will arise.

The type of the centrifuge and the condition for the isolation used in the present invention are not particularly limited, provided that the centrifugation can be accomplished so that the mother liquid is sufficiently eliminated.

The crystalline parahydroxybenzoic acid anhydride of the present invention shows larger particle size and contains less fine particles compared to that obtained by the conventional method. The crystalline parahydroxybenzoic acid anhydride of the present invention is improved in the flowability, wherein it shows the angle of repose of 30 to 45° and the compression ratio equal to or less than 10%, while the conventional crystalline product shows the angle of repose of 45 to 60° and the compression ratio from 10 to 30%. The crystalline parahydroxybenzoic acid anhydride of the present invention is, therefore, easy to handle, especially to deliver, fill, and store, as the frying of the powders during work is prevented.

Further, the crystalline parahydroxybenzoic acid anhydride of the present invention are characterized in that the specific surface area of the particles that can pass through a 100 mesh (150 μm) sieve and can not a 140 mesh (106 μm) sieve is equal to or less than 0.3 m$^2$/g.

This means that crystalline parahydroxybenzoic acid anhydride obtained by drying crystalline parahydroxybenzoic acid monohydrate is an aggregate consisting of fine crystals, which has a large specific surface area and is prone to generate powder dust. In contrast, the crystalline parahydroxybenzoic acid anhydride of the present invention having the same particle size mainly consists of large crystals and generates less powder dust.

Here, "particles that can pass through a 100 mesh sieve and can not a 140 mesh sieve" only represents the condition for measuring the specific surface area, and the crystalline parahydroxybenzoic acid anhydride of the present invention is not limited to the particles having a particle size in that range.

Further, as described above, the parahydroxybenzoic acid of the present invention is obtained as crystalline anhydride, and therefore the water content after centrifugation is low, i.e., equal to or less than 10%. In other words, the crystalline parahydroxybenzoic acid anhydride obtained by the process of the present invention, even before dried, shows quite low water content. It allows that the undried crystalline parahydroxybenzoic acid anhydride is used directly as a starting material for manufacturing, for example, parahydroxybenzoic acid ester, because it is not necessary to be substantially anhydrous.

The detail of the present invention is explained by means of the following Examples and Comparative Examples.

EXAMPLE 1

The following is Example in which parahydroxybenzoic acid was precipitatated with acid and isolated at a temperature equal to or above the transition temperature of parahydroxybenzoic acid.

Two thousand grams of aqueous solution of potassium parahydroxybenzoate (the composition of the solution is shown in Table 1) was put into a 3 L flask, and heated to 60° C. Under the same temperature, parahydroxybenzoic acid was precipitated with acid, wherein the pH was adjusted to 2.8 with 110 g of 73% aqueous sulfuric acid solution. The step of precipitation with acid and the following step of isolation were performed at a temperature from 60 to 65° C. throughout the steps.

The suspension of parahydroxybenzoic acid obtained by the precipitation with acid was filtered by using a centrifuge at 60° C. Following the filtration, the residue was washed with 150 g of ion-exchanged water of 65° C. using the centrifuge, and the water used for washing was removed by centrifugation. As a result, 132.5 g of crystalline parahydroxybenzoic acid anhydride was obtained. The water content measured by Karl Fischer's method was 2.9%. The resulting crystalline product was dried with airflow at 70° C., and 128.7 g of crystalline parahydroxybenzoic acid anhydride was obtained.

TABLE 1

| Ingredient | Ratio (% by weight) |
| --- | --- |
| Potassium parahydroxybenzoate | 13.5 |
| Parahydroxybenzoic acid | 0.5 |
| Potassium sulphate | 3.2 |
| Water | 82.8 |

EXAMPLE 2

The following is Example in which parahydroxybenzoic acid was precipitated with acid at a temperature below the transition temperature of parahydroxybenzoic acid, the precipitates were heated to dissolve, and then the parahydroxybenzoic acid was precipitated and isolated at a temperature equal to or above the transition temperature.

Two thousand grams of aqueous solution of potassium parahydroxybenzoate (the composition of the solution is shown in Table 1) was put into a 3 L flask, and parahydroxybenzoic acid was precipitated with acid, wherein the pH was adjusted to 2.8 with 106.5 g of 73% aqueous sulfuric acid solution at 20° C.

The suspension of parahydroxybenzoic acid obtained by the precipitation with acid was heated to 90° C. to give an aqueous solution of parahydroxybenzoic acid. The solution was cooled to 60° C. at a rate of 0.5° C./min, and filtered by using a centrifuge at 60° C. Following the filtration, the residue was washed with 132 g of ion-exchanged water of 65° C. using the centrifuge, and the water used for washing was removed by centrifugation. As a result, 127.8 g of crystalline parahydroxybenzoic acid anhydride was obtained. The water content measured by Karl Fischer's method was 3.1%. The resulting crystalline product was dried with airflow at 70° C., and 123.9 g of crystalline parahydroxybenzoic acid anhydride was obtained.

EXAMPLE 3

The following is Example in which parahydroxybenzoic acid in an aqueous solvent was heated to a temperature equal to or above the transition temperature of parahydroxybenzoic acid to dissolve, and then precipitated and isolated at a temperature equal to or above the transition temperature.

Two hundred grams of parahydroxybenzoic acid and eight hundred grams of ion-exchanged water were put into a 1 L flask, and heated to 95° C. to give a solution of parahydroxybenzoic acid. The solution was cooled to 60° C. at a rate of 0.5° C./min, and filtered by using a centrifuge at 60° C. As a result, 165.3 g of crystalline parahydroxybenzoic acid anhydride was obtained. The water content measured by Karl Fischer's method was 2.1%. The resulting crystalline product was dried with airflow at 70° C., and 161.9 g of crystalline parahydroxybenzoic acid anhydride was obtained.

EXAMPLE 4

The following is Example in which, using 10% methanol as the aqueous solvent, parahydroxybenzoic acid was heated to a temperature equal to or above the transition temperature to dissolve, and then precipitated and isolated at a temperature equal to or above the transition temperature.

Three hundred grams of parahydroxybenzoic acid and one thousand and five hundred grams of 10% aqueous methanol solution were put into a 2 L flask, and heated to 80° C. to give a 10% aqueous methanol solution containing parahydroxybenzoic acid. The solution was cooled to 60° C. at a rate of 0.5° C./min, and filtered by using a centrifuge at 60° C. As a result, 184.0 g of crystalline parahydroxybenzoic acid anhydride was obtained. The water content measured by Karl Fischer's method was 4.5%. The resulting crystalline product was dried with airflow at 70° C., and 174.9 g of crystalline parahydroxybenzoic acid anhydride was obtained.

COMPARATIVE EXAMPLE 1

The following is Comparative Example in which parahydroxybenzoic acid was crystallized with acid and isolated at a temperature below the transition temperature of parahydroxybenzoic acid.

Two thousand grams of the aqueous solution of potassium parahydroxybenzoate used in Example 2 was put into a 3 L flask, and under the temperature of 30° C., parahydroxybenzoic acid was precipitated with acid, wherein the pH was adjusted to 2.8 with 106.5 g of 72% aqueous sulfuric acid solution. The suspension was filtered using a centrifuge at 30° C. Following the filtration, the residue was washed with 200 g of ion-exchanged water of 30° C. on the centrifuge, and the water used for washing was removed by centrifugation. As a result, 238.6 g of crystalline parahydroxybenzoic acid monohydrate was obtained. The water content measured by Karl Fischer's method was 17.8%. The resulting crystalline product was dried with airflow at 70° C., and 196.1 g of crystalline parahydroxybenzoic acid anhydride was obtained.

COMPARATIVE EXAMPLE 2

The following is Comparative Example in which parahydroxybenzoic acid in an aqueous solvent was heated to a temperature equal to or above the transition temperature of parahydroxybenzoic acid to dissolve, and precipitated and isolated at a temperature below the transition temperature.

Two hundred grams of parahydroxybenzoic acid and eight hundred grams of ion-exchanged water were put into a 1 L flask, and heated to 95° C. to give an aqueous solution of parahydroxybenzoic acid. The solution was cooled to 30° C. at a rate of 0.5° C./min, and filtered at 30° C. As a result, 216.4 g of crystalline parahydroxybenzoic acid monohydrate was obtained. The water content measured by Karl Fischer's method was 16.2%. The resulting crystalline product was dried with airflow at 70° C., and 190 g of crystalline parahydroxybenzoic acid anhydride was obtained.

COMPARATIVE EXAMPLE 3

The following is Comparative Example in which parahydroxybenzoic acid was heated to a temperature equal to or above the transition temperature using 10% methanol as the aqueous solvent, and then precipitated and isolated at a temperature below the transition temperature.

Three hundred grams of parahydroxybenzoic acid and one thousand and five hundred grams of 10% aqueous methanol solution were put into a 2 L flask, and heated to 80° C. to give a 10% aqueous methanol solution containing parahydroxybenzoic acid. The solution was cooled to 25° C. at a rate of 0.5° C./min, and filtered by using a centrifuge at 25° C. As a result, 324.9 g of crystalline parahydroxybenzoic acid monohydrate was obtained. The water content measured by Karl Fischer's method was 16.6%. The resulting crystalline product was dried with airflow at 70° C., and 268.4 g of crystalline parahydroxybenzoic acid anhydride was obtained.

The size distribution, particle characteristics and specific surface area of the parahydroxybenzoic acid obtained in Examples 1 to 3 and Comparative Examples 1 to 3 are shown in Table 2, 3, and 4, respectively.

TABLE 2

Size Distribution

| | Size Distribution (%) | | | | | | | Average Particle Size (μm) |
|---|---|---|---|---|---|---|---|---|
| | 20M on ~710 μm | 32M on 710~500 μm | 46M on 500~297 μm | 83M on 297~170 μm | 145M on 170~100 μm | 200M on 100~74 μm | 200M pass 74 μm~ | |
| Example 1 | 5.4 | 24.7 | 55.3 | 12.6 | 1.9 | 0.1 | 0.1 | 350 |
| Example 2 | 4.4 | 44.7 | 39.6 | 8.9 | 1.7 | 0.1 | 0.6 | 389 |
| Example 3 | 4.5 | 57.2 | 28.7 | 6.1 | 2.1 | 0.6 | 0.7 | 417 |
| Example 4 | 7.7 | 30.1 | 36.1 | 18.9 | 5.5 | 1.0 | 1.0 | 351 |
| Comparative Example 1 | 0 | 0 | 1.0 | 44.3 | 46.3 | 6.1 | 2.4 | 130 |
| Comparative Example 2 | 0.3 | 0.4 | 8.4 | 39.4 | 34.1 | 10.3 | 7.1 | 141 |
| Comparative Example 3 | 0 | 0 | 3.1 | 33.4 | 49.6 | 10.9 | 3.1 | 125 |

TABLE 3

Powder Characteristics

| | Example 1 | Example 2 | Example 3 | Example 4 | Comparative Example 1 | Comparative Example 2 | Comparative Example 3 |
|---|---|---|---|---|---|---|---|
| Angle of Repose (deg.) | 38.9 | 36.3 | 36.3 | 38.7 | 47.9 | 48.5 | 57.1 |
| Compression Ratio (%) | 6.3 | 2.7 | 1.6 | 7.9 | 21.6 | 13.5 | 25.8 |
| Aerated Bulk Density (g/cc) | 0.540 | 0.719 | 0.727 | 0.536 | 0.501 | 0.550 | 0.441 |
| Packed Bulk Density (g/cc) | 0.576 | 0.739 | 0.739 | 0.582 | 0.639 | 0.636 | 0.594 |

TABLE 4

Specific Surface Area

| Example 1 | Example 2 | Example 3 | Example 4 | Comparative Example 1 | Comparative Example 2 | Comparative Example 3 |
|---|---|---|---|---|---|---|
| 0.09 $m^2/g$ | 0.07 $m^2/g$ | 0.06 $m^2/g$ | 0.07 $m^2/g$ | 0.61 $m^2/g$ | 0.75 $m^2/g$ | 0.82 $m^2/g$ |

The results demonstrate that the crystalline parahydroxybenzoic acid anhydride obtained by the process of the present invention shows large particle size, and small angle of repose, compression ratio, and specific surface area.

Figure 2:
FIG. 2 is the micrograph showing crystalline parahydroxybenzoic acid obtained in Comparative Example 2.

FIGS. 1 and 2 are micrographs showing the crystalline parahydroxybenzoic acid obtained in Example 3 and Comparative Example 2, respectively.

The crystalline parahydroxybenzoic acid anhydride obtained by the process of the present invention shows large particle size and superior powder characteristics.

Powder characteristics were measured as follows.

Size Distribution and Average Particle Size

The size distribution and the average particle size were measured using a shaker (Iida Seisaku Sho ES-65) according to the following method.

Size Distribution

The sample is weighted and then is sequentially screened with sieves having aperture of 710 μm, 500 μm, 297 μm, 170 μm, 100 μm and 74 μm in this order, and the residue on each sieve is weighed. Firstly, the sample is screened with a sieve having aperture of 710 μm at 230 rpm for 10 minutes. The amount of the residue on the sieve is weighted and the ratio by weight (wt %) of the amount to that of the starting sample is calculated. The sample having passed through the 710 μm sieve is then screened with a sieve having aperture of 500 μm in the same manner as above. These steps are repeated successively and at the end, the amount of the sample having passed through the 74 μm sieve is weighed. The wt % of the amount of the residue on each sieve and that of the sample having passed through the 74 μm sieve, to that of the starting sample, are calculated.

Average Particle Size

The average particle size is calculated based on the result of the size distribution obtained as above according to the following formula:

Average Particle Size (μm)=(710×wt % of the residue on the 710 μm sieve/100)+(500×wt % of the residue on the 500 μm sieve/100)+(297×wt % of the residue on the 297 μm sieve/100)+ (170×wt % of the residue on the 170 μm sieve/100)+(100×wt % of the residue on the 100 μm sieve/100)+(74×wt % of the residue on the 74 μm sieve/100)+(40×wt % of the sample having passed through the 74 μm sieve/100).

Powder Characteristics

The angle of repose, bulk density, and compression ratio are measured using Powder Tester (Type PT-N, Hosokawa micron Co.) according to the manufacturer's instruction.

Angle of Repose

The sample is shaken on a standard sieve (10 mesh) to be allowed to fall through a funnel and the angle of repose is measured by means of the pouring method. The value of angle of repose is small for powders with good flowability and that is large for powders with a tendency of adhesion and aggregation.

Aerated Bulk Density

The sample is shaken on a sieve to be allowed to fall into a standard container through a shout, and then the standard container is weighted to determine the aerated bulk density Packed Bulk Density The sample is filled into a standard container, the container is tapped from a given height for given times and then, bulk density of the sample packed by tapping impact is determined.

Compression Ratio

Compression ratio is the value obtained from the aerated bulk density and packed bulk density according to the following formula: (packed bulk density−aerated bulk density)/packed bulk density×100. The compression ratio is the most important factor in view of flowability of powders, and a large value of compression ratio represents poor flowability.

Specific Surface Area

Specific surface area is determined for a sample that can pass through a 100 mesh (150 μm) sieve and can not a 140 mesh (106 μm) sieve using Monosorb (QUANTACHROME).

Measurement Condition

Method: Single point BET method

Carrier gas: 30 vol. % nitrogen and 70 vol. % herium

Gas flow rate: 15 cc/min

Vacuum condition: 100° C., 10 min

Micrograph

Micrographs were taken using VH-6200 (KEYENCE CORP.). Each scale corresponds to 0.2 mm.

INDUSTRIAL APPLICABILITY

The crystalline parahydroxybenzoic acid anhydride obtained by the process of the present invention can be widely used as a starting material of liquid crystal polymers or preservatives for cosmetics, medicines and the like.

What is claimed is:

1. A process for preparing crystalline parahydroxybenzoic acid anhydride, comprising the step of precipitating and isolating parahydroxybenzoic acid in an aqueous solvent at a temperature equal to or above the transition temperature of parahydroxybenzoic acid.

2. The process for preparing crystalline parahydroxybenzoic acid anhydride according to claim 1, wherein the precipitating and isolating step is performed at a temperature which is in the range from the transition temperature to the transition temperature +30° C.

3. A process for preparing crystalline parahydroxybenzoic acid anhydride, comprising the step of precipitating and isolating parahydroxybenzoic acid with acid from a solution of parahydroxybenzoate in an aqueous solvent at a temperature equal to or above the transition temperature of parahydroxybenzoic acid.

4. A process for preparing crystalline parahydroxybenzoic acid anhydride, comprising the steps of: precipitating parahydroxybenzoic acid in an aqueous solvent with acid, heating the parahydroxybenzoic acid precipitates to dissolve the same, and re-precipitating and isolating the parahydroxybenzoic acid at a temperature equal to or above the transition temperature of parahydroxybenzoic acid.

5. A process for preparing crystalline parahydroxybenzoic acid anhydride, comprising the steps of:

providing;

a liquid solution of parahydroxybenzoic acid in an aqueous solvent by heating a suspension of parahydroxybenzoic acid monohydride in an aqueous solvent:

precipitating crystalline parahydroxybenzoic acid anhydride by keeping said solution at a temperature equal to or above the transition temperature of parahydroxybenzoic acid; and isolating the crystalline parahydroxybenzoic acid anhydride at a temperature equal to or above the transition temperature of parahydroxybenzoic acid.

6. A process for preparing crystalline parahydroxybenzoic acid anhydride, comprising the steps of:

provide a suspension of parahydroxybenzoic acid monohydride in an aqueous solvent, converting parahydroxybenzoic acid monohydride to parahydroxybenzoic acid anhydride by heating the suspension to a temperature equal to or above the transition temperature of parahydroxybenzoic acid, and isolating the crystalline parahydroxybenzoic acid anhydride at a tempertaure equal to or above the transition temperature of parahydroxybenzoic acid.

7. The process for preparing crystalline parahydroxybenzoic acid anhydride according to claim 1, 2, 3, 4, 5 or 6, wherein the aqueous solvent is water and the transition temperature of parahydroxybenzoic acid is 52 to 54° C.

8. Crystalline parahydroxybenzoic acid anhydride prepared by the method of claim 1, wherein particles of parahydroxvbenzoic acid anhydride can pass through a 100 mesh (150 μm) sieve and can not pass through a 140 mesh (106 μm) sieve, and the specific surface area of the particles is equal to or less than 0.3 m2/g.

9. The crystalline parahydroxybenzoic acid anhydride according to claim 8, wherein the angle of repose is equal to or less than 45°.

10. The crystalline parahydroxybenzoic acid anhydride according to claim 8 or 9, wherein the compression ratio calculated according to the following formula is equal to or less than 10%: (packed bulk density-aerated bulk density)/packed bulk density×100.

* * * * *